(12) United States Patent
Giasson et al.

(10) Patent No.: US 8,457,772 B2
(45) Date of Patent: Jun. 4, 2013

(54) METHOD FOR PLANNING A DENTAL COMPONENT

(75) Inventors: David Giasson, Quebec (CA);
Philippe-Armand Laberge, Quebec (CA); Marc Bedard, Pont Rouge (CA); Urban Nilsson, Hålta (SE); Per-Olof Karlsson, Alingsås (SE); Anna Persson, Stockholm (SE)

(73) Assignee: Biocad Medical, Inc., Quebec (CA)

( * ) Notice: Subject to any disclaimer, the term of this patent is extended or adjusted under 35 U.S.C. 154(b) by 544 days.

(21) Appl. No.: 12/703,632

(22) Filed: Feb. 10, 2010

(65) Prior Publication Data

US 2011/0196524 A1   Aug. 11, 2011

(51) Int. Cl.
| | | |
|---|---|---|
| *G06F 19/00* | (2006.01) | |
| *A61C 3/00* | (2006.01) | |
| *A61C 13/00* | (2006.01) | |
| *A61C 5/00* | (2006.01) | |
| *A61C 8/00* | (2006.01) | |
| *A61C 11/00* | (2006.01) | |
| *A61C 9/00* | (2006.01) | |
| *A61C 5/08* | (2006.01) | |

(52) U.S. Cl.
USPC .......... 700/98; 433/24; 433/167; 433/215; 433/75; 433/173; 433/201.1; 433/213; 433/214; 433/218

(58) Field of Classification Search
USPC ............. 700/98; 433/24, 167, 215, 75, 173, 433/201.1, 213, 214, 218, 233
See application file for complete search history.

(56) References Cited

U.S. PATENT DOCUMENTS

| | | | |
|---|---|---|---|
| 2003/0039389 A1* | 2/2003 | Jones et al. | 382/154 |
| 2004/0081938 A1* | 4/2004 | Chishti et al. | 433/24 |
| 2005/0186540 A1* | 8/2005 | Taub et al. | 433/223 |
| 2006/0115793 A1* | 6/2006 | Kopelman et al. | 433/215 |
| 2006/0122719 A1* | 6/2006 | Kopelman et al. | 700/98 |
| 2006/0275737 A1* | 12/2006 | Kopelman et al. | 433/213 |
| 2007/0233299 A1* | 10/2007 | Kopelman et al. | 700/98 |
| 2008/0261165 A1* | 10/2008 | Steingart et al. | 433/24 |
| 2009/0248184 A1* | 10/2009 | Steingart et al. | 700/98 |
| 2010/0003635 A1* | 1/2010 | Feith | 433/75 |
| 2010/0281370 A1* | 11/2010 | Rohaly et al. | 715/719 |

* cited by examiner

*Primary Examiner* — Sean Shechtman
*Assistant Examiner* — Jason Lin
(74) *Attorney, Agent, or Firm* — Knobbe, Martens, Olson & Bear, LLP.

(57) ABSTRACT

Presented herein are methods and devices for designing dental components, such as physical models of a patient's anatomy, crowns and bridges. An operator of a prosthetic designing system can receive information, such as from a scanner, which provides information on the topology of the patient's dentition. The operator can use this information to design a custom prosthetic to fit the patient. Part of the designing process involves using a finish line defined for a preparation as a segmentation line for a physical die corresponding to the preparation, and using a path of draw line as an insertion axis line for a dental prosthetic.

18 Claims, 14 Drawing Sheets

METHOD FOR PLANNING A DENTAL COMPONENT

BACKGROUND

1. Field of the Inventions

The present application generally relates to the field of prosthodontics and more particularly to a method and apparatus for planning a dental component.

2. Description of the Related Art

A tooth supported artificial dental prosthetic, such as a crown or bridge, can cover portions of a tooth surface and is normally fabricated away from the patient's mouth, in a lab, and then installed in the mouth by the dental practitioner. A tooth preparation, as used herein, is a tooth that has been reshaped for accepting dental prosthetics. To achieve a strong fitting of a dental prosthetic, it is important for the surface of the tooth preparation to coincide closely with the mating surface of the dental prosthetic.

Typically, for a dental crown, after diagnosing that a patient needs a dental prosthetic, the dentist grinds down the tooth to be reconstructed and takes two impressions and a wax bite of the patient's jaws. Based on the impressions, a technician prepares a corresponding cast. The prepared cast typically comprises two parts corresponding to the upper and lower jaw. One of the parts includes a representation of the preparation. The representation of the preparation is referred to as a die; which is a physical representation of the preparation. The die is often sectioned from the overall cast of the jaw so that it can be individually viewed and manipulated.

A finish line (also known as "preparation line") is defined as the apical limit of the preparation and the margin of the prosthetic typically ends on it. After the prepared cast of the patient's dentition is created, the finish line can be manually marked by the lab technician in ink on the die. An insertion line is the direction of insertion of the prosthetic onto the preparation. The insertion line is chosen, in part, so as to avoid collisions with adjacent teeth. The finish line and path of insertion line are important parameters used in constructing and implanting the crown or bridge.

In recent years, dental prosthetic design has been accomplished increasingly using computer systems and 3D computer graphics or CAD (computer-aided design) software. These systems allow a dentist, dental technician, or other operator to design dental prosthetics for individual patients. These individual prosthetic designs are often called "situations," "dental plans," or "prosthetic plans." The prosthetic plans that are made in the 3D or CAD software are typically based on the scans of the patient's teeth, gums, and bone structure and other system constraints. Once the dentist has loaded all of the relevant data for the patient, the plan can be refined. A virtual three-dimensional (3D) image of the cast is obtained e.g. in a manner as described in international publication No. WO97/03622, or in international publication No. WO00/08415.

U.S. Pat. No. 5,417,572 discloses a computer-based method for extracting a finish line for designing an artificial crown. Amounts of variation of data representing the shape of a preparation are determined, and a train of points is extracted from the amounts of variation. The finish line for designing the artificial crown is determined, based on thus displayed train of points. U.S. Pat. No. 7,488,174 discloses a computer-based method for constructing a crown to be fitted on a preparation in a subject. The method comprises defining a finish line to obtain finish line data and employing the finish line data in constructing the crown. The finish line is determined by providing a three-dimensional digital data relating to the patient's dentition and generating first finish line data which is updated with second finish line data obtained from a dental practitioner.

As noted above, the finish line is an important design constraint for the final prosthetic. An accurate finish line enables optimal mating between the preparation and the crown. Thus, the more precisely the 3D or CAD model reproduces the anatomy of the mouth in the areas to be treated, the more accurate will be the spatial position as will be the static and dynamic relationships within the mouth after treatment.

Even with these advanced 3D or CAD software systems, a physical model of the patient's jaw and the preparation is typically needed. The physical model is used to check the fit between the crown (which can be designed on the 3D or CAD software system) and the preparation. In addition, the interaction between the crown and the adjacent jaw can be checked. U.S. Pat. No. 7,220,124 discloses a method of machining a physical model based upon a 3D computer graphics or CAD representation of the impressions of the patient. By machining the physical model, certain improvements in accuracy can be achieved as compared to traditional plaster cast based models which are cast directly from the impressions of the patient jaw. In a similar manner, U.S. Pat. No. 7,384,266 also discloses a method of machining a physical model from 3D computer graphics or CAD representation of the impressions of the patient. In this case, the physical model can be divided up into more than one part. For example, the model can be segmented into individual tooth components.

While the above described 3D or CAD software systems and methods of creating a physical model are useful, in practice, they can be cumbersome for a dental practitioner to use. For example, they often require the practitioner to make multiple decisions and require several individual steps in order to create the desired physical model. In a similar, manner 3D or CAD software systems require multiple steps to create a prosthetic. There also remains a need to eliminate the cast physical model while still maintaining dimensional accuracy, particularly in prosthetic applications which place a higher demand on accuracy than other applications such as orthodontic applications.

SUMMARY

An aspect of at least one of the embodiments disclosed herein includes the realization that the finish line defined for the tooth preparation can be used as the cut line of the die and/or the margin line for the prosthetic, and the path of draw line defined during the production of the die and/or on a virtual model can be used as the insertion axis line of the coping and bridge, crown and/or die. Presented herein are methods, systems, devices, and computer-readable media for designing dental prosthetics.

Thus, in accordance with at least one of the embodiments disclosed herein includes a method of making a dental component. The method includes obtaining, at a computer system, patient specific data regarding a patient's oral anatomy, including three-dimensional surface data of a dental preparation. The computer system can be used to produce a three-dimensional model of the patient's oral anatomy using the data. A first aspect of the patient's oral anatomy is defined using the three-dimensional model. A first aspect of a first dental component is defied using the first aspect of the patient's oral anatomy. A first aspect of a second dental component is defined using the first aspect of the patient's oral anatomy.

In accordance with at least another embodiment, a method of making a dental component comprises obtaining, at a computer system, patient specific data regarding a patient's oral anatomy, including three-dimensional surface data of a dental preparation. A virtual three-dimensional model of the patient's oral anatomy is produced using the data. A finish line is defined on a virtual model of the preparation. A segmentation line for a die is defined using the finish line of the preparation. A margin for a dental prosthetic is defined using the finish line.

In accordance with at least another embodiment, a method of making a dental component comprises obtaining, at a computer system, patient specific data regarding a patient's oral anatomy, including three-dimensional surface data of a dental preparation. A virtual three-dimensional model of the patient's oral anatomy is produced using the data. A draw line is defined using the virtual three-dimensional model. An insertion axis line of a dental prosthetic is defined using the draw line. A segmentation surface of a die is defined using the draw line.

In accordance with at least another embodiment, a computer system for use in constructing a tooth die and tooth product to be fitted on the tooth die comprises a scanner for creating digital data representing the surface topology of a physical object and one or more computers each comprising one or more processors and one or more memories. The one or more computers being configured to accept the digital data for use in producing a three-dimensional representation of a patient's dentition, generate a removable tooth die, define a finish line of a preparation and superimposing an image of the finish line on an image of the dentition, define a draw line of the tooth die and superimposing an image of the draw line on an image of the dentition; and accept input from an operator, said input being used by the system to define a segmentation line of the tooth die, accept input from an operator, said input being used by the system to define an insertion axis line of a dental prosthetic. The finish line can be used as the segmentation line and the draw line is used as the insertion axis line of the dental prosthetic.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the inventions herein disclosed. These and other embodiments will become readily apparent to those skilled in the art from the following detailed description having reference to the attached figures, the invention not being limited to any particular disclosed embodiment(s).

DETAILED DESCRIPTION OF SPECIFIC EMBODIMENTS

As noted above, it is important to have an accurate physical model of the patient's mouth in order to produce an accurate restoration. It would be advantageous if such a physical model would be functionally equivalent or better than the current plaster models used by practitioners. Such a physical model would advantageously include a separate piece or die corresponding to the preparation. In addition, the steps required to create the physical model and/or prosthetics from a 3D software or CAD program are preferably kept to a minimum.

Various embodiments disclosed herein can be used to create such a physical model. For example, in one embodiment, a dental practitioner in a 3D or CAD environment can design a virtual model by using a finish line of a preparation to create a segmentation line for a die and/or a final prosthetic and/or by using a path of draw line of a die as an insertion axis line (or a basis for an insertion line) for a prosthetic that can be designed in a 3D or CAD environment (or vice versa). After the virtual model is created, a physical model corresponding to the virtual model created in the 3D or CAD environment of the patient's dentition can be made. In addition, a prosthetic having a margin line corresponding (and/or based upon) a finish line and/or an insertion line corresponding to or based upon the path of draw line can be created. In some embodiments, a ditch can be added to the virtual die and/or physical die below the finish line. In some embodiments, a ditch can be added to the virtual model and/or physical model of the anatomy (e.g., soft tissue) surrounding the virtual die and/or physical die. In such embodiments, the ditch can allow the accuracy to be checked more easily on the physical model and/or virtual model.

In one embodiment, the virtual three-dimensional (3D) model is created from a 3D image of the impressions taken of the patient's mouth (i.e., a physical negative teeth model). The physical negative model may be used to provide a digital negative representation of the patient's dentition, from which a digital positive representation of the patient's dentition may be digitally obtained. Alternatively, the physical negative teeth model may be used to prepare a physical positive teeth model, from which a digital positive teeth representation can be produced. In some embodiments, the virtual three-dimensional image may be manipulated by the operator as described below to design the physical model from the virtual three-dimensional image.

Figure 1:
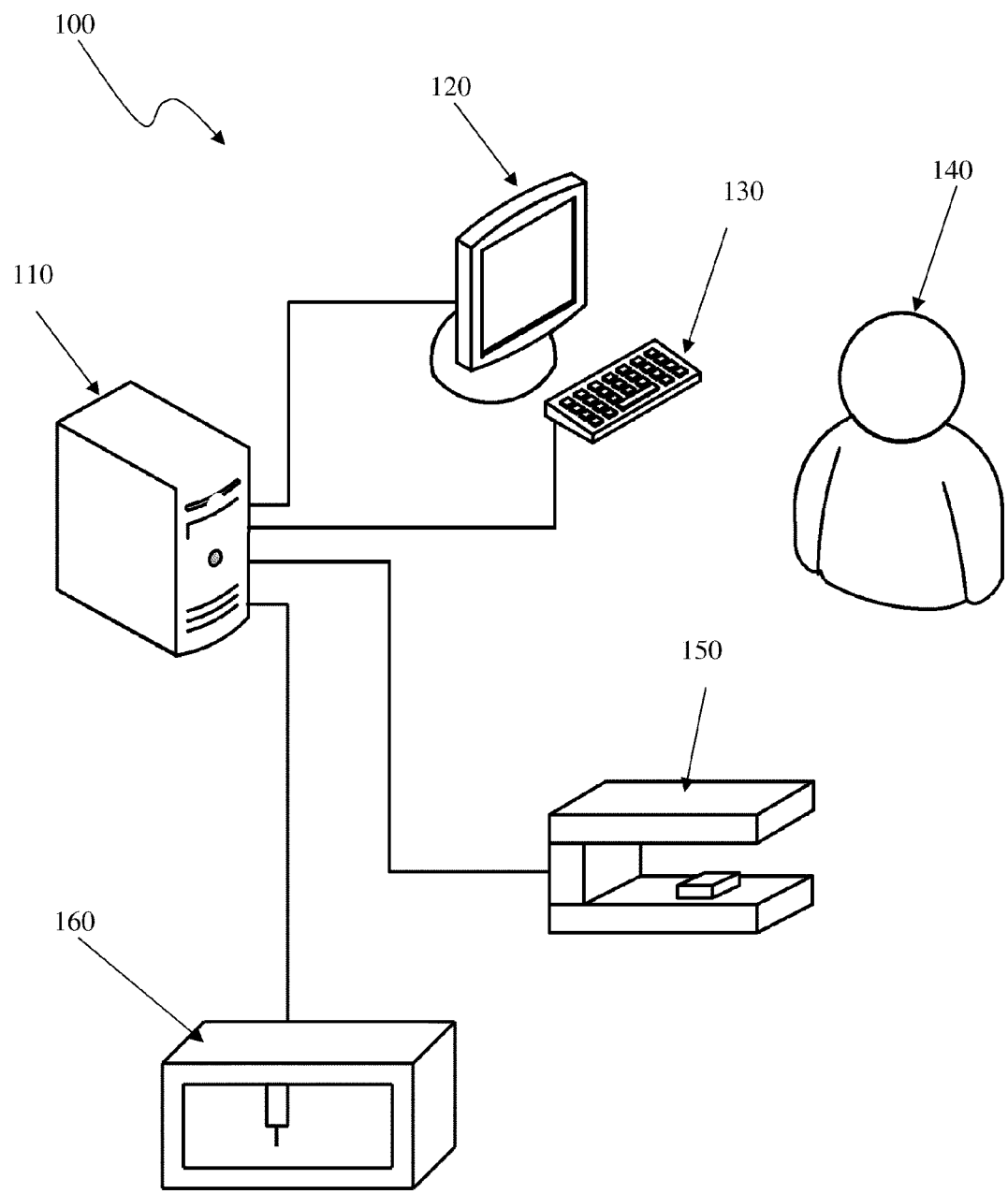
FIG. 1 is schematic diagram of a system for dental planning, according to an embodiment of the invention.

FIG. 1 illustrates an embodiment of a system 100 for dental planning. The system 100 can include one or more computers 110 coupled to one or more displays 120, one or more input devices 130, and one or more scanners 150, such as a 3D scanner. An operator 140, who may be a dentist, dental technician, trained practitioner or other person, may plan dental prosthetics and/or a physical jaw model using system 100 by manipulating the one or more input devices 130, which may be a keyboard and/or a mouse (not pictured). In some embodiments, while working on the dental plan, the operator 140 may see the dental plan on the display 120. The display 120 may include two or more display regions, each of which display a different aspect of the dental plan. For example, in some embodiments, the display 120 may show a case designer for indicating and modifying the general dental plan, a list of the scans that need to take place for the dental plan and their statuses, a list of products that will be needed for the dental plan and an indication of the viabilities of using those products for the dental plan, a video or image of an object in the scanner 150, and/or a rendering of the 3D surface just scanned, possibly with the 3D surfaces of previous scans as well. The display 120 may also have an area that would allow the operator 140 to input patient(s) data, which the operator could input using input devices 130, such as a keyboard and mouse. As will be described below, in an embodiment, the display 120 or a different display can display a virtual model of a patient's oral anatomy. The display 120 can also be used to identify a finish line of a virtual representation of a preparation. This virtual finish line can be used on segmentation line for a virtual die and/or a virtual final prosthetic that can be viewed on the display 120. In certain arrangements, the display 120 can be used to view and/or create a draw line, which can be used as a path of draw line for a virtual die and/or an insertion axis line for a virtual prosthetic that can be viewed on the display 120. Other aspects of the processes described below can also be viewed on the display 120.

In some embodiments, the computer 110 can include one or more processors, one or more memories, and one or more communication mechanisms. In some embodiments, more than one computer 110 may be used to execute the modules, methods, and processes discussed herein. Additionally, the modules and processes herein may each run on one or multiple processors, on one or more computers; or the modules herein may run on dedicated hardware. The input devices 130 may include one or more keyboards (one-handed or two-handed), mice, touch screens, voice commands and associated hardware, gesture recognition, or any other means of providing communication between the operator 140 and the computer 110.

The display 120 may be a 2D or 3D display and may be based on any technology, such as LCD, CRT, plasma, projection, etc. The scanner 150 may be a 2D or 3D scanner. In some embodiments, 3D scanning in scanner 150 is accomplished using time-of-flight calculations, triangulation, conoscopic holography, structured light, modulated light, computed tomography, microtomography, magnetic resonance imaging, or any appropriate technology or technique. In some embodiments, 3D scanner may use x-rays, visible light, laser light, ultrasound radiation, or any other appropriate radiation or technology. In some embodiments, the 3D scanner may use stereoscopy, photometry, silhouetting, or any other appropriate technique. In some embodiments, the 3D scanner can use touch probe scanning or any other physical measurement technique.

In some embodiments, the system 100 can include a modeling apparatus 160 that is used to construct a physical model utilizing digital data received from computer 110. In some embodiments, a Computer Numerical Control (CNC) milling machine can be used. In other embodiments, any other CAM (Computer Aided Manufacturing) technology that can produce a physical model out of virtual data can be used. For example, in one embodiment, the physical model can be created using stereolithography or injection modeling techniques.

In some embodiments of the illustrated system, the physical negative teeth model is translated into a digital representation of the patient's dentition through scanning the physical negative teeth model. In some embodiments, the operator 140 can be prompted to place a first object such as an impression, wax-up, implant replica, etc. into the scanner 150. When prompted to do so by the display 120, the operator 140 may put the next needed object, such as a dental plan wax-up or a plaster model, into the scanner 150. In various embodiments, the scanner 150 can then proceed with the scanning of the teeth impression or model.

After the virtual image is generated, the display is typically a computerized display, provided with software permitting the technician to visualize the virtual image from different angles. As will be appreciated, the invention is not limited to any specific display means and any means for presenting the image such as, for example, in a printed format, on a computer display screen, etc., may be employed in accordance with some embodiments.

It should be appreciated that while the system 100 illustrated in FIG. 1 shows the various component interconnected together to the same computer 110, in other embodiments, several different computer systems can be used. In such systems, data can be transferred to different computers via the internet or physically through storage media. For example, the scanner 150, display 120 and modeling apparatus can each be connected to separate computers.

Figure 2:
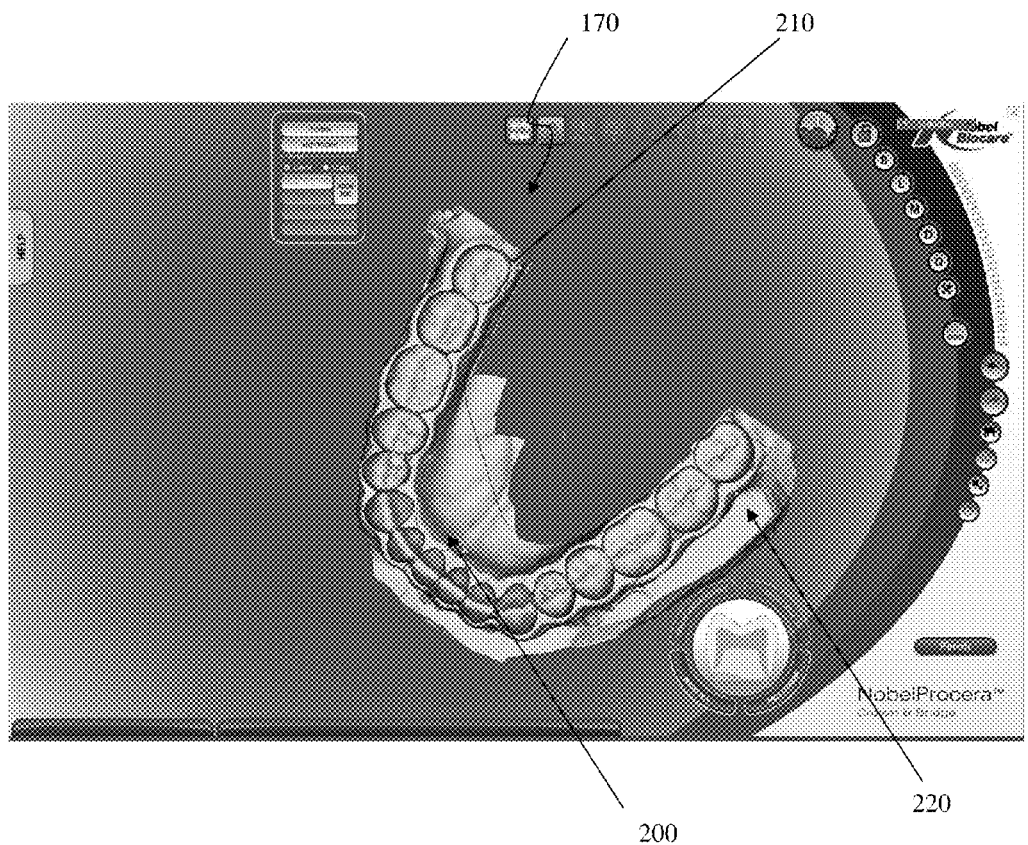
FIG. 2 is a top perspective view of a model of a patient's dentition showing a cut line for trimming the model, according to an embodiment of the invention.

With reference to FIG. 2, a working model 200 of a positive image of an impression is shown. In one procedure, the display includes tools for generating a cut line 210. The cut line 210 can be used to define undesired or excess portions 220 from the scanning procedure. These excess portions 220 can be cut away from the working model 200 before proceeding further. In this manner, excess data can be eliminated from the working model 200. In one embodiment, the cut line 210 can be automatically defined by the computer, or the cut line 210 can be created by manually defining various points along the perimeter of the cut line 210. After the cut line 210 has been defined, the tooth arch can be aligned in a correct occlusal plane. The procedure can be repeated for the positive image of the opposing jaw. The virtual models for the opposing jaws can then be aligned on the same screen to define the proper alignment between the upper and lower models of the jaw. One technique for aligning the virtual models of the upper and lower jaws is described in EP Application No. 09004003.1, filed Mar. 20, 2009, the entirety of which is hereby incorporated by reference herein.

Figure 3:
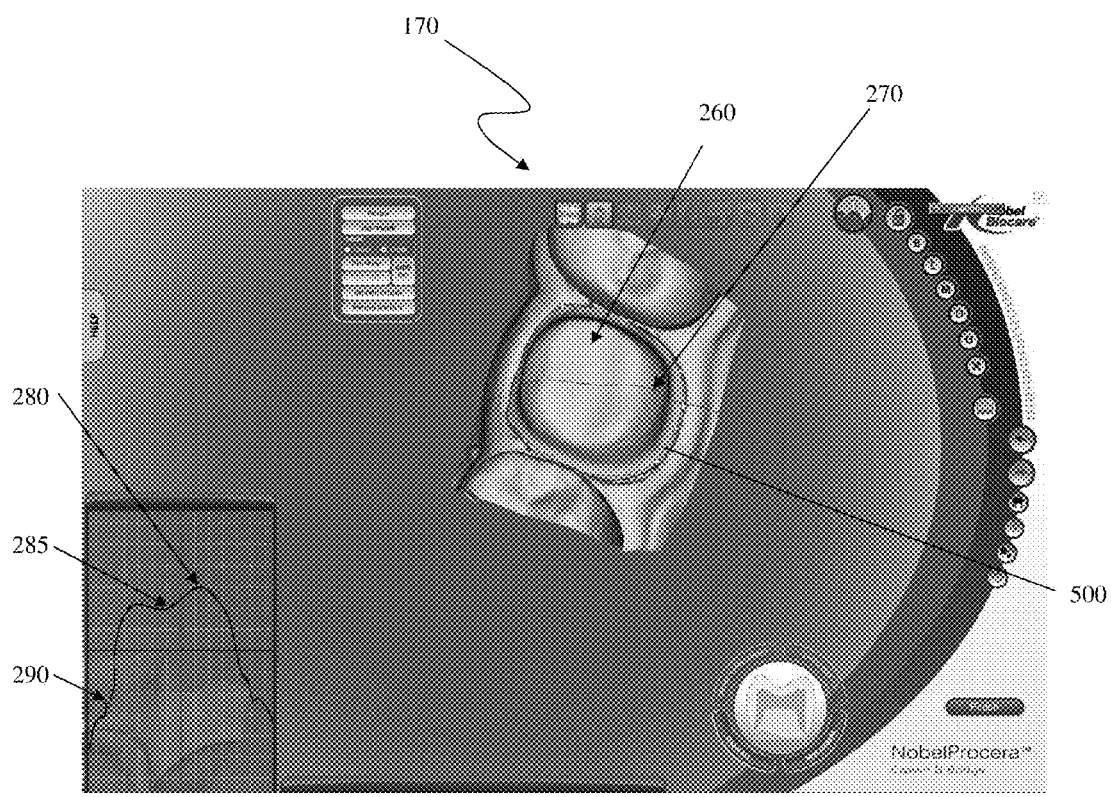
FIG. 3 is a close-up top perspective view of a model of a patient's dentition illustrating a finish line of a preparation, according to an embodiment of the invention.

As illustrated in FIG. 3, it can be advantageous to define a finish line 500 on the dentition image 170, which by definition, is the apical limit of an image of the preparation 260. A finish line 500 can be generated on the preparation 260 in a manual or a semi-automated or a fully automated manner. In preferred embodiments, the finish line 500 can be superimposed on the dentition image and displayed on a suitable display medium.

Figure 4:
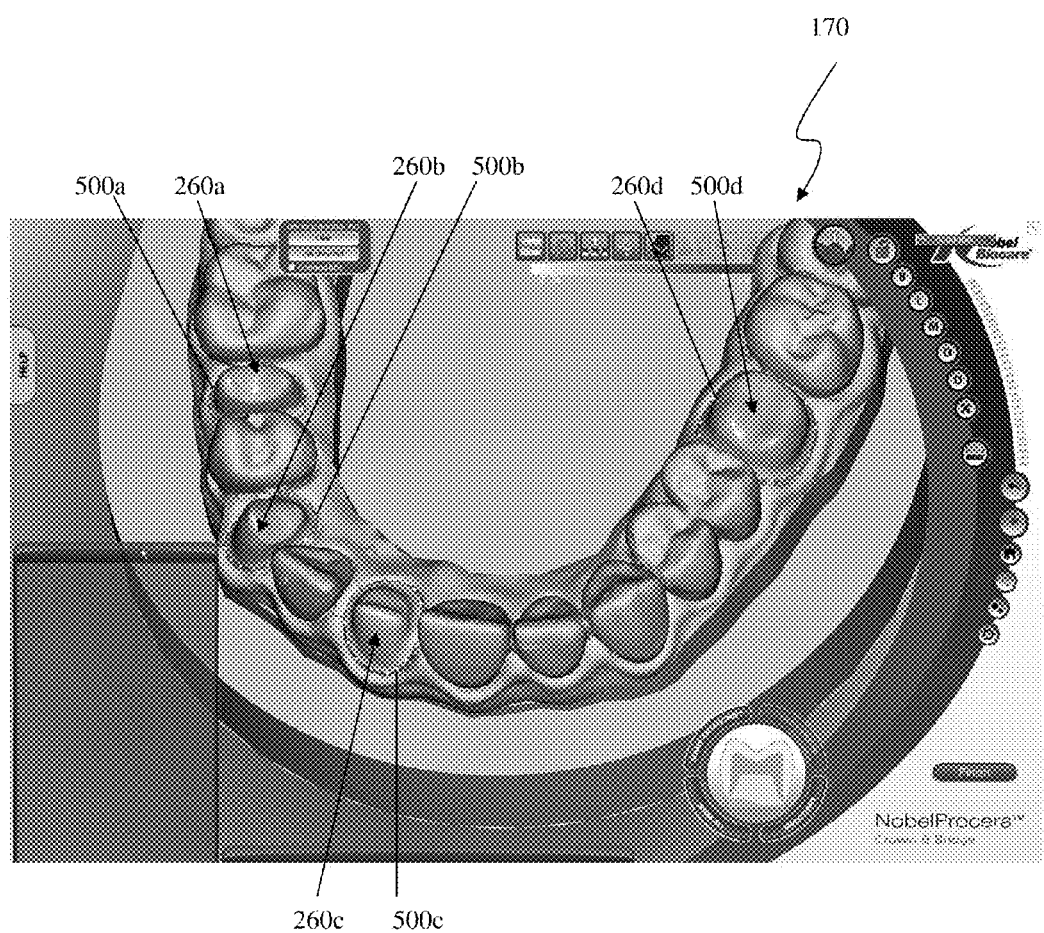
FIG. 4 is a top perspective view of a model of a patient's dentition illustrating the finish lines of several abutment teeth, according to an embodiment of the invention.
Figure 5:
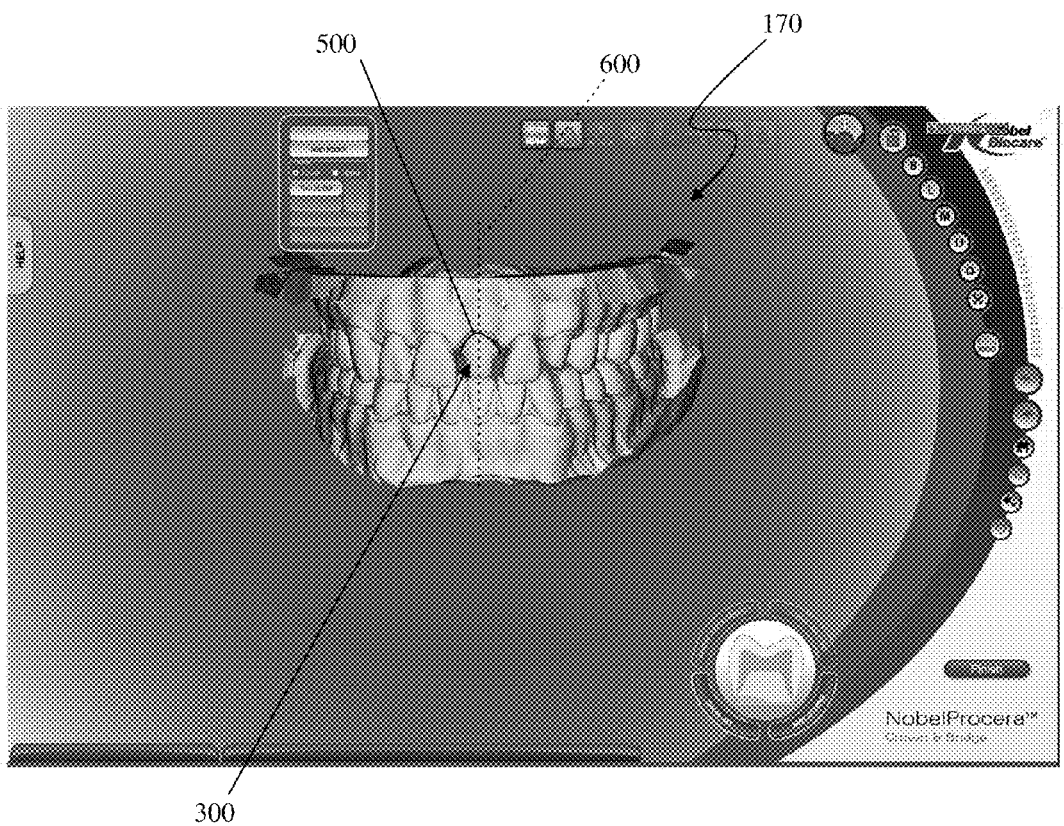
FIG. 5 is a side elevational view of a model of a patient's dentition illustrating the occlusion of opposing teeth.

FIGS. 3 and 4 show examples of such a display. In the illustrated embodiment, the preparation 260 is seen with its neighboring teeth and with a finish line 500 drawn as a continuous line on the apical limit of preparation 260. The operator can be provided with a 3D image of the preparation 260 and its surroundings wherein the finish line 500 is marked, for example, by a colored line. FIG. 4 illustrates a dentition image 170 with multiple preparations 260a, 260b, 260c and 260d, each having a different finish line 500a, 500b, 500c and 500d, respectively. In some embodiments, the dentition image 170 can include teeth of the jaw opposite the preparation region. In some embodiments, the dentition image 170 can also include all teeth of both jaws, as illustrated in FIG. 5.

In some embodiments, the operator can be allowed to enlarge the image and to manipulate it for better viewing of the dentition image 170. The dentition image 170, and particularly the region thereof that includes the preparation 260, is preferably manipulable such that the dentition image 170 may be displayed and visualized from different angles. The operator can further be provided with 2D images of cross-sections of the preparation 260. In the embodiment illustrated in FIG. 3, the cross-section is taken along line 270 and the 2D image is illustrated in the window in the lower left corner of the screen. The 2D image allows the operator to visualize the peaks 280 and valleys 285 along the specific cross-sectional line 270. The 2D image also shows the intersection point 290 at which the finish line intersects the cross-section, which can help the operator to more accurately define the finish line.

In some embodiments the computer 110 can include a software utility for generating data representative of at least a portion of said finish line 500. Rather than manually drawing or marking the finish line 500 in the virtual 3D environment, the finish line 500 can be generated by the computer 110. The computer 110 can perform calculations based on data indicating the 3D shape of the surface of the preparation to produce the finish line 500. In another embodiment, a combination of the manual marking and computer generated data can be used to mark the finish line 500 in the virtual environment. For example, in some embodiments, the generation of the finish line 500 data can be obtained in a manual or semi-automatic manner. For example, the finish line 500 may be drawn by moving a cursor, by moving a stylus on a touch-sensitive screen or pad, etc. In an embodiment, the finish line 500 is drawn by indicating a series of dots while the software then automatically connects the dots into one continuous finish line 500.

The finish line 500 data can be updated or adjusted by operator input. The updating can comprise defining a portion of the finish line 500 not defined by the computer (for example, in a 'knife edge' case) or changing a portion of the finish line 500. The updated data is further imposed on the dentition image.

Figure 6:
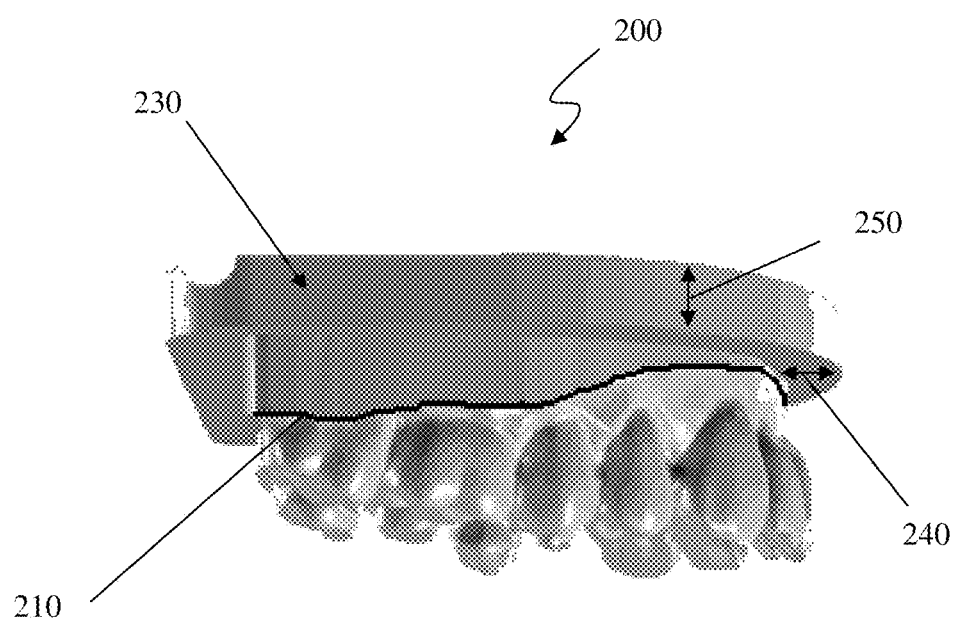
FIG. 6 is a side perspective view of a model of a patient's dentition, according to an embodiment of the invention.

To create a base of the working model 200, the cut line 210 can be extended to merge the aligned tooth arch together with a base plate 230 that can typically have a U-shape, as illustrated in FIG. 6. In preferred embodiments, the minimum distance between the cut line 210 and the base plate 230 is approximately 0.5 mm, but with enough total height in order to fit a steering part and pin of the preparation. Preferably, the minimum buccal distance 240 outside the cut line 210 is approximately 5 mm and the height of the base plate 250 is approximately 5 mm. In other embodiments, however, the distance between the cut line 210 and base plate 230, the buccal distance 240 and the base plate height 250 can be greater than or less than the measurements of the preferred embodiment.

Figure 7:
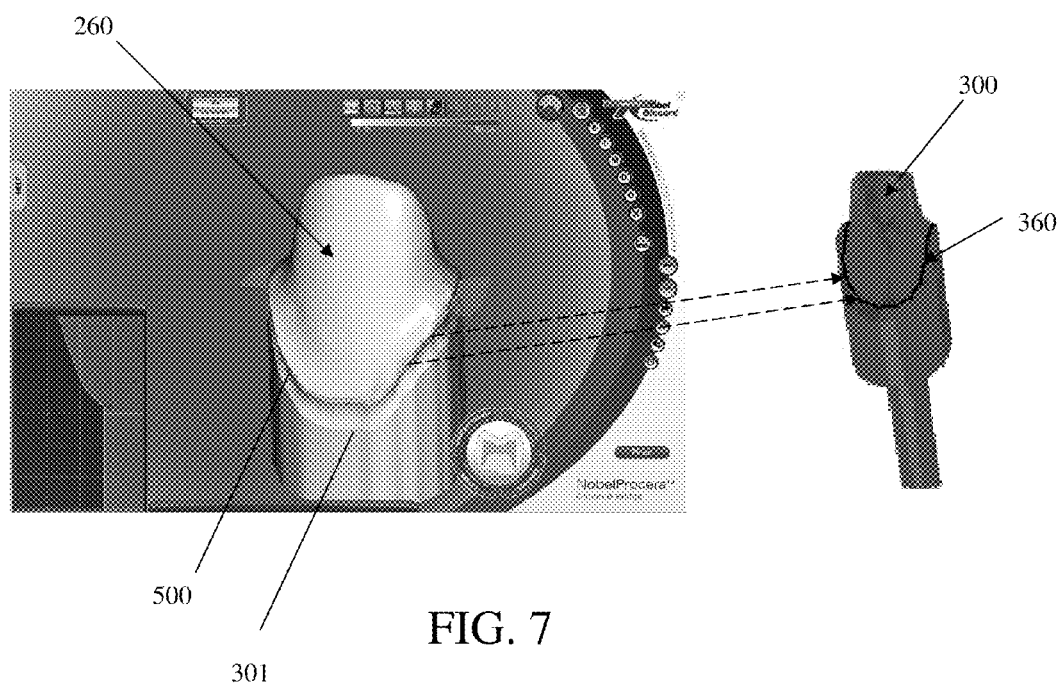
FIG. 7 is a close-up top perspective view of a model of a patient's dentition illustrating a finish line of an preparation used for a dental preparation, according to an embodiment of the invention.
Figure 8:
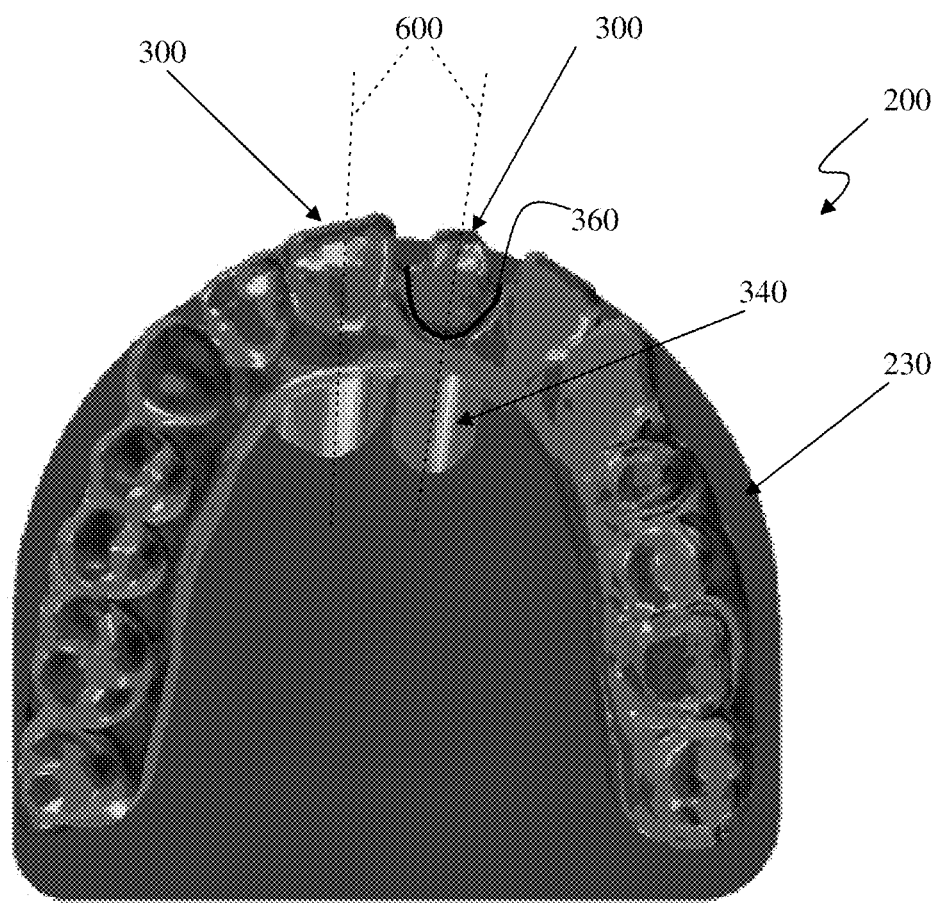
FIG. 8 is a top plan view of a model of a patient's dentition illustrating a removable preparation coupled with the model, according to an embodiment of the invention.

In the working model 200, the finish line 500 can be used as the segmentation line 360 in defining a die 300, as illustrated in FIG. 7, by extending the segmentation line 360 into the base plate 230, as illustrated in FIG. 8. In another embodiment, the finish line 500 is used as the segmentation line by using the finish line 500 as an initial proposal for the segmentation line 360 and/or as a basis for determining the segmentation line 360.

A path of draw line 600 is defined as an axis along which the segmentation line 360 can be extended to form the die 300. In other words, the draw line 600 is the direction and angle for the extension of the segmentation line 360 to form the die 300. Extension of the segmentation line 360 into the model 200 also defines a die hole 340. Thus, the path of draw line 600 is the direction and angle for the extension of the finish line 500 into the model 200, which defines the die 300 and die hole 340. The die 300 is preferably removable from the rest of the model 200. The draw line 600 is also selected such that the die 300 when removed from the rest of the model does not abut against the adjacent teeth structures.

In some embodiments, the operator can modify or adjust the segmentation line 360 and/or draw line 600 of the die 300 before defining the die 300 for a customized fit with the model 200. In other embodiments, the finish line 500 and/or draw line 600 can be used to define the die 300 without modification.

With continued reference to FIG. 8, in some situations, the path of draw line 600 can have a high degree of angulation with respect to the base plate and/or a longitudinal axis of adjacent teeth; e.g. in the frontal area the thickness of the working model 200 around the die hole 340 may be too thin or even protrude outside the tooth arch. In order to have a minimum wall thickness, material can be added to the model 200.

Figure 9:
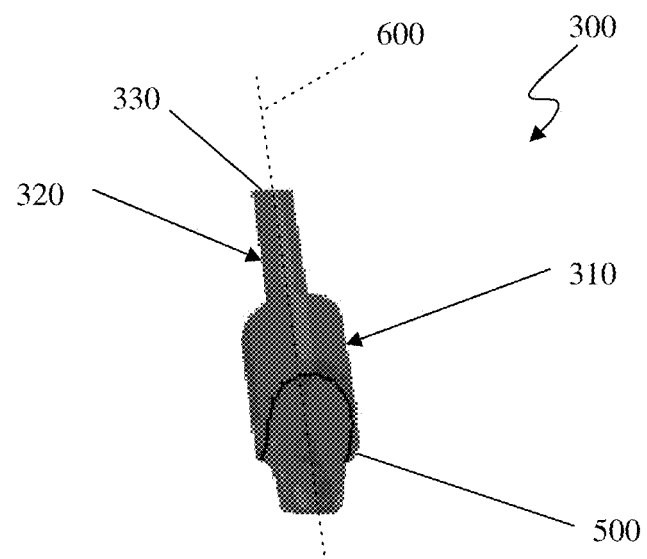
FIG. 9 is a perspective view of a removable preparation, according to an embodiment of the invention.

With reference to FIG. 9, in a preferred embodiment, the height of a steering part 310 is a minimum of approximately 2 mm. In other embodiments, the height of the steering part 310 can be less than approximately 2 mm. The structure of the die 300 can continue in a pin 320, which in a preferred embodiment has a diameter of approximately 3 mm. In other embodiments, the diameter of the pin 320 can be less than or greater than 3 mm, but preferably less than the diameter of the steering part 310. The pin 320 preferably has a minimum height of approximately 6 mm so that the pin 320 can be grasped by the user, but in some embodiments, the pin 320 can have a height less than approximately 6 mm. For example, the height of the pin 320 can be relatively short such that it does not extend to the top of the model 200 and the die hole 340 may not extend to the base plate 230. In the illustrated embodiment, the steering part 310 can extend along the same or substantially the longitudinal axis as the path of draw line 600. That is, a longitudinal axis of the steering part 310 can be based, at least in part, upon the draw line 600.

Figure 10:
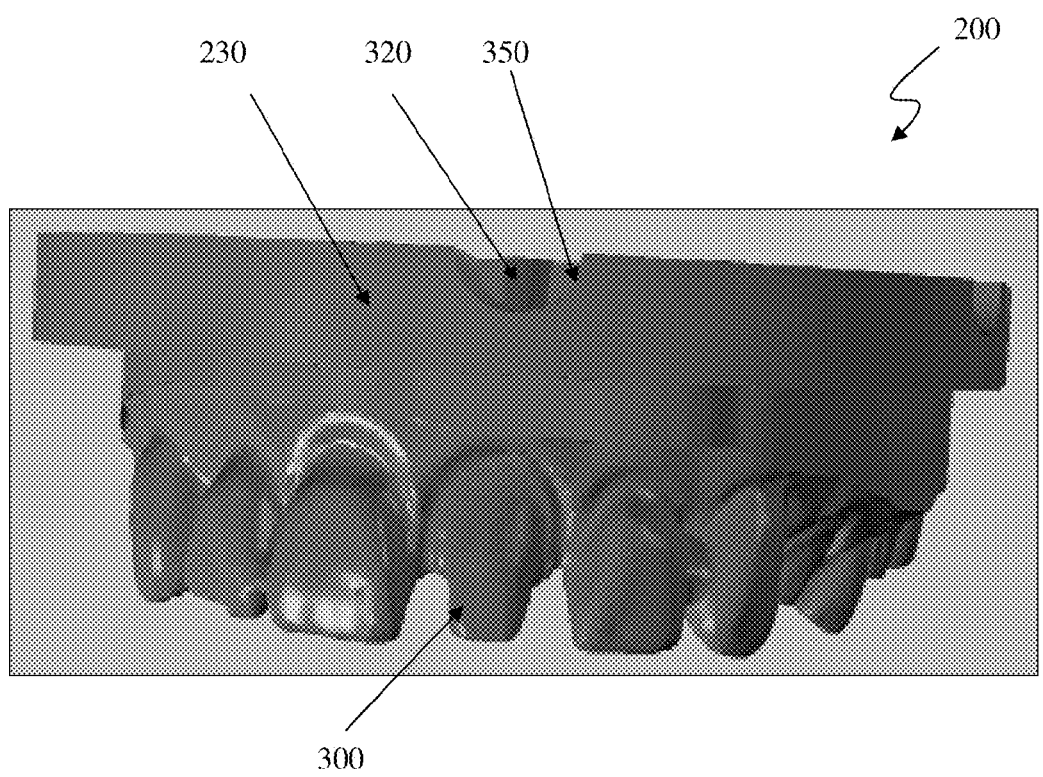
FIG. 10 is a front elevational view of a model of a patient's dentition illustrating a removable preparation coupled with the model, according to an embodiment of the invention.

FIG. 10 illustrates a virtual die 300 assembled with a base of the working model 200. In some embodiments, the apical end of the pin 330 is generally flush with the top surface of a base plate 230, as in the embodiment illustrated in FIG. 10. In the case where the distance between the cut line 210 and the base plate 230 is insufficient to enable the pin 320 to have a minimum height, the extension of the cut line 210 can be increased. The model 200 can also be moved within the occlusal plane to expand or reduce the length of the pin 300.

If a ditch (not illustrated) on the model 200 is desired, the die hole 340 can be automatically ditched. In one embodiment, the ditch on the model is laterally offset from the margin 500 or segmentation line 360. In this manner, the ditch can be positioned on the soft tissue of the physical or virtual model. The ditch can be present in both the virtual model and/or the physical model. In addition, or in the alternative, as shown in FIG. 7, the virtual die 260 and/or physical die 300 can include a ditch 301. In the illustrated embodiment, the ditch 301 can be offset below the finish line 500 and/or segmentation line 360. The ditch 301 can make using the die easier. In some embodiments, when the model is converted to a physical model with a ditch, the ditch can allow the operator to check the accuracy of the prosthetic easier on the physical model. In situations when the soft tissue of the patient is below the finish line 500 and the anatomical part of the tooth is of interest, a segmentation line 360 marking the boundary between the soft tissue and the tooth can be defined and used for manufacturing of the preparation hole 340 in the model 200. In these situations, the ditch in the hole is typically not included on the model.

In some embodiments, the preparation hole 340 can have a hollow 350 on the back side that can make it easier to remove the die 300 from the working model 200. In a preferred embodiment, the diameter of the hollow is approximately 5 mm with a depth of approximately 2 mm and can be in the shape of a half sphere. In other embodiments, the diameter and depth of the hollow can be any appropriate size and shape. To remove the die 300 from the model 200, the pin 320 can be pressed from the back to eject the die 300 through the preparation hole 340.

Figure 11:
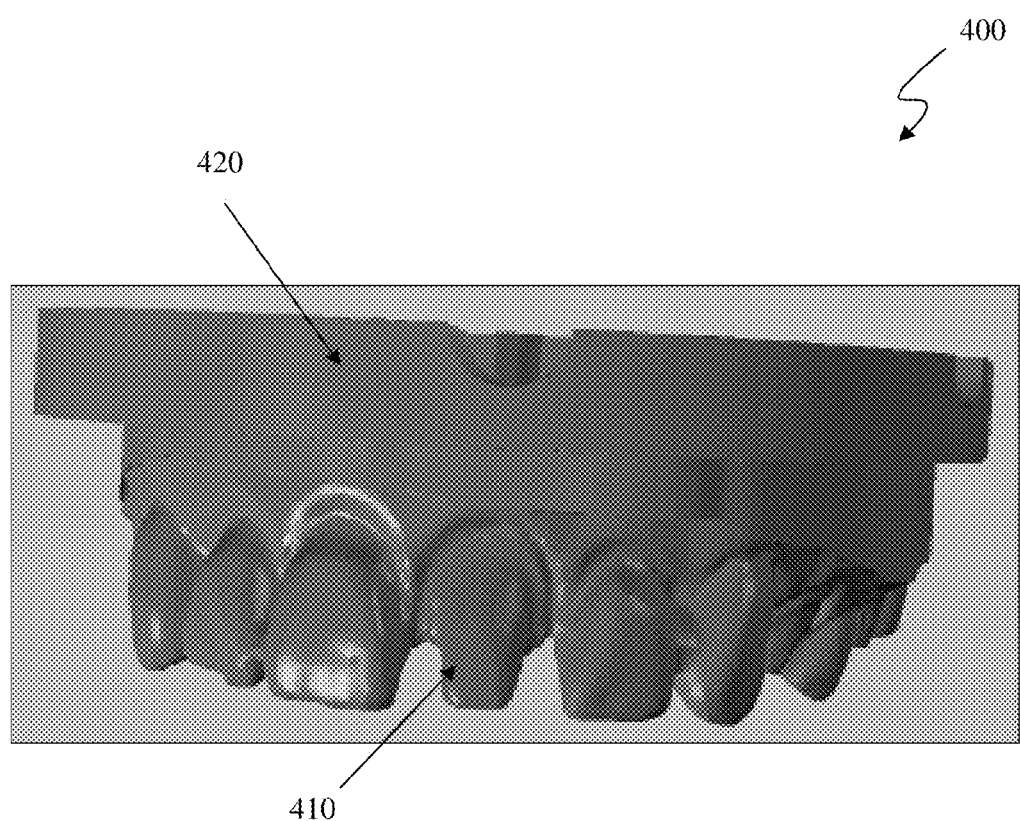
FIG. 11 is a front view perspective of a physical model of a patient's dentition illustrating a removable preparation coupled with the model, according to an embodiment of the invention.

FIG. 11 illustrates an example of a physical model 400 of the patient's dentition. A physical die 410 is coupled with the physical base plate 420 of the physical model 400. In one embodiment, the physical model 400 is created from the modeling apparatus 160 based upon the virtual die 300 and model described above.

Once the die 300 is defined, a physical model 410 of the die 300 can be made for use as a template by the operator in custom making a tooth prosthetic 700. In preferred embodiments, the data containing the information for the virtual die 300 can be sent to an offsite manufacturing location where the physical die 410 can be made, such as with a Computer Numerical Controlled (CNC) machine.

As described above, the path of draw line 600 is defined as an axis along which the segmentation line 360 can be extended to form the die 300, and more specifically to form the steering part 310 of the die 300. As with defining the finish line 500, the draw line 600 can be generated on the model in a manual or a semi-automated or a fully automated manner. In a preferred embodiment, the draw line 600 can be superimposed on the dentition image 170 and displayed on a suitable display medium. In some embodiments, the operator can be allowed to enlarge the image and to manipulate it for better viewing of the model. The dentition image 170, and particularly the region thereof that includes the preparation 260, is preferably manipulable such that the dentition image 170 may be displayed and visualized from different angles.

Figure 12:
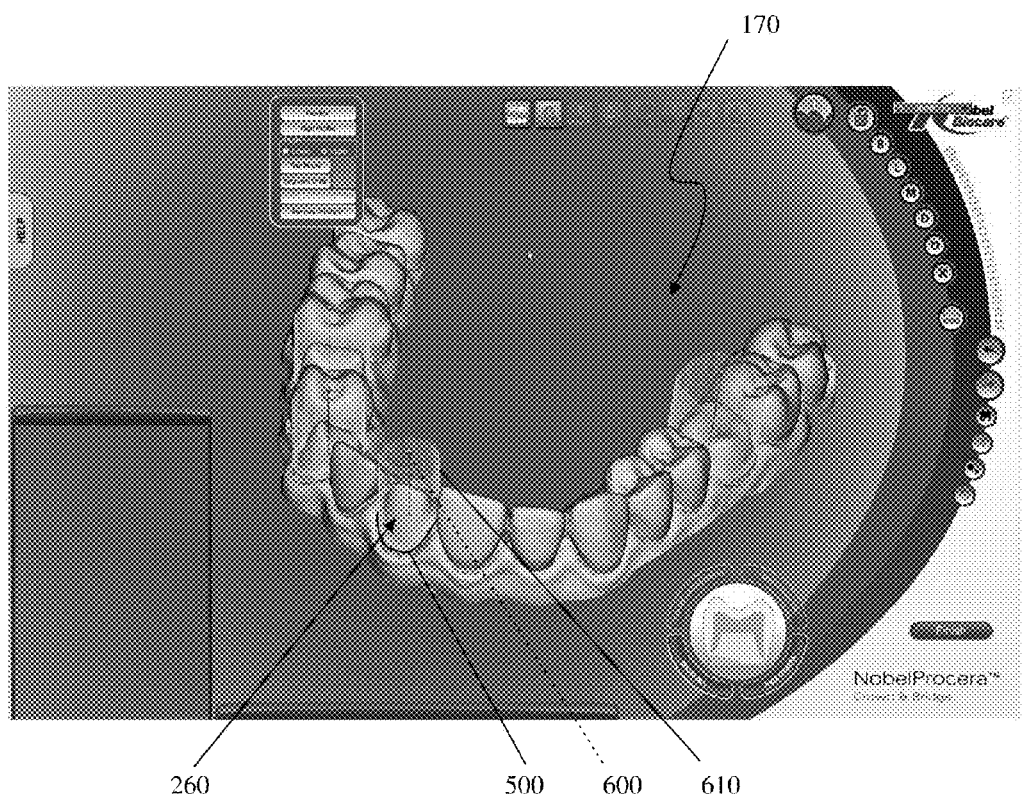
FIG. 12 is a top perspective view of a model of a patient's dentition illustrating the path of draw lines of several abutment teeth, according to an embodiment of the invention.

FIG. 12 shows an example of the draw line 600 shown on a display medium with the representation of the dentition image 170. A preparation 260 is seen with its neighboring teeth. A surface 610 is extended upward from the finish line 500 to ensure that the path of draw does not interfere with the sides of the neighboring teeth. The path of draw line 600 is the central axis of the extended surface 610. In the illustrated embodiment, the operator is provided with a 3D image of the preparation 260 and its surroundings wherein the draw line 600 is marked, for example, by a colored line. In some embodiments, the representation of the patient's dentition can include teeth of the jaw opposite the preparation region. In some embodiments, the virtual teeth model can also include all teeth of both jaws, as illustrated in FIG. 5.

The draw line 600 data can be updated or adjusted by the user's input. The updating can comprise adjusting the angle or position of the draw line 600. The updated data is further imposed on the dentition image 170. In preferred embodiments, as the draw line 600 is adjusted, the extended surface also changes to show the adjusted path of draw.

Figure 13:
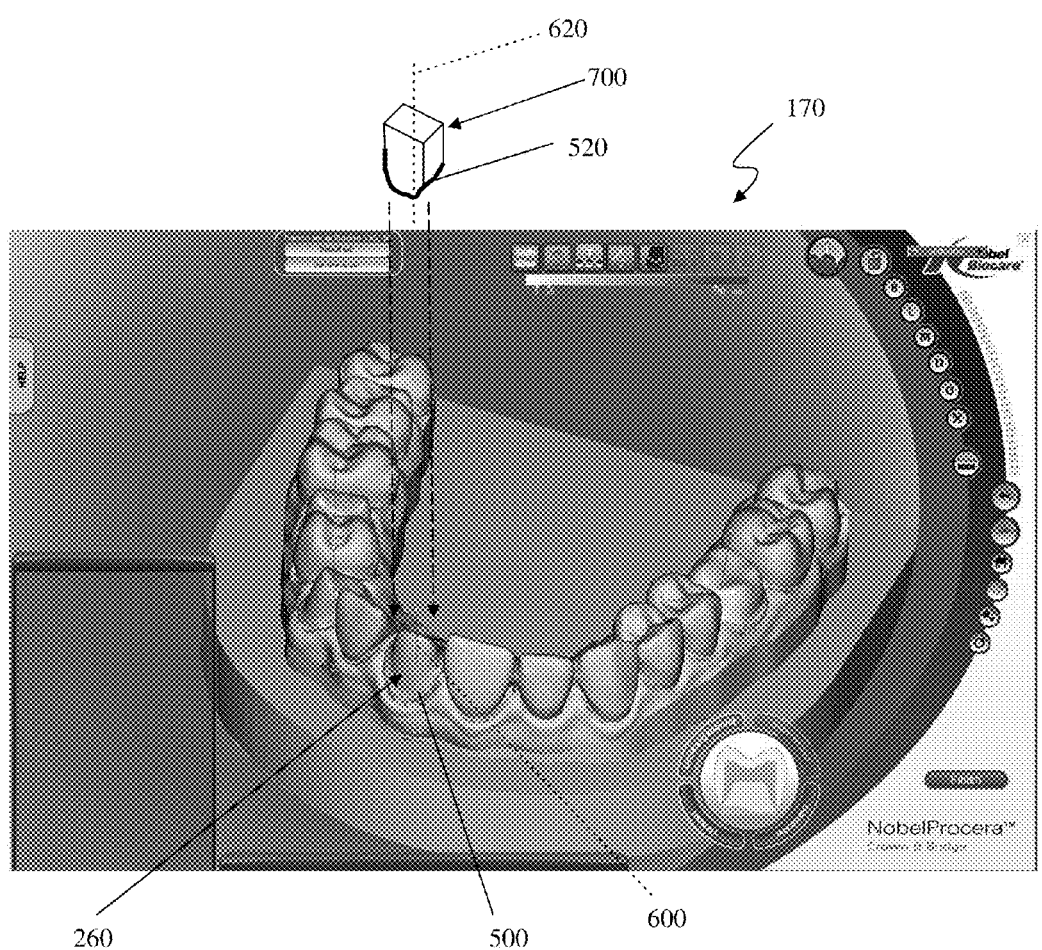
FIG. 13 is a top perspective view of a model of a patient's dentition illustrating an insertion axis line of a prosthetic and a preparation, according to an embodiment of the invention.

With reference to FIG. 13, in accordance with some embodiments disclosed herein, the draw line 600 can be used as the insertion axis line 620 of the prosthetic 700. The insertion axis line 620 of the prosthetic 700 can be defined as the angle and orientation at which the prosthetic 700 can be inserted onto the preparation 260 such that the dental components do not interfere with the neighboring teeth. In some embodiments, the draw line 600 is used as the insertion axis line 620 by basing the insertion axis 620 on the draw line 600 or using the draw line 600 as an initial proposal for the insertion axis 620 and then, for example, modifying the insertion axis 620.

Using the draw line 600 as the insertion axis line 620 defines a path along which the prosthetic 700 can be attached and ensures that the prosthetic 700 fits properly with the preparation 260. The method of using the draw line 600 as the insertion axis line 620 is particularly advantageous for bridges, where each tooth prosthetic in the bridge must have complimentary insertion axis lines for the bridge to properly fit on the preparation. For example, because the tooth prosthetics in a bridge are typically rigidly connected together, the entire bridge must be inserted onto the abutment teeth along the same angle and orientation. To ensure that the bridge fits properly, the insertion axis lines of each tooth prosthetic must have complimentary angles and orientations. To accomplish this, the draw lines of the preparations for the prosthetics can be defined so that they have complimentary angles and orientations, and then the draw lines can be used to define the insertion axis lines of the bridge.

By using the draw line 600 as the insertion axis line 620, the height and size of the prosthetic 700 can be adjusted for optimal adjustment to the jaw occlusion. In some embodiments, the technician can modify the insertion axis line 620 before manufacturing the die 300 and/or prosthetic 700. Modification of the insertion axis line 620 can be desirable to provide a custom fit or appearance for the prosthetic 700 with the die 300 and/or preparation 260. In other embodiments, the insertion axis line 620 can be collinear with the draw line 600 of the preparation 260. That is, one advantage of this arrangement is that a design specification for one component (e.g., die) that is based on patient specific data can be used for a design specification of a second component (e.g., prosthetic) based on the same patient specific data. In some embodiments, the design specification for the one component is used at least as a proposal for a design specification of the second component.

In some embodiments, the data regarding the finish line 500 and/or draw line 600 can be transferred to another module in the dental planning system 100, or transferred out to a separate program for use in designing the prosthetic 700. The prosthetic module, or separate program, can include the impression data or can be configured to accept the impression data, wherein the prosthetic module or separate program can use the collected data to design a prosthetic 700. The collected data can include, inter alia, information about the contours of the preparation 260, the finish line data. The prosthetic module can use the collected data to calculate other data for the production of the prosthetic 700. For example, the prosthetic module can define an offset to compensate for the layer of cement between the prosthetic 700 and the preparation 260, the internal surface of the prosthetic 700 that mates with the preparation 260, and the shape and size of the external surface of the prosthetic 700 to match the surrounding teeth of the patient's dentition.

In some embodiments, the operator may use the dentition image 170 with the finish line 500 and the draw line 600 marked therein by the operator to construct a virtual prosthetic to be fitted over the virtual tooth preparation. Once a good prosthetic fitting is determined, the virtual prosthetic data can be used to construct the actual physical prosthetic. The guidance may be a visual guidance, although, in accordance with some embodiments, digital data representative of the three dimensional structure of the virtual prosthetic is generated and this may be fed into a computer-controlled apparatus that automatically constructs the prosthetic based on such data. In some embodiments, a computer-controlled apparatus can be used to automatically construct the prosthetic based on the digital data representation of the virtual prosthetic.

Preferably, the operator can use the raw impression data or the dentition image 170 to design the prosthetic. In some embodiments, the working model 200 can be used in designing the prosthetic 700, however, the raw impression data is preferable because the extraneous data in the model 200 can interfere with the fit and design of the prosthetic 700.

In some embodiments, the user can include a ditch on the working model 200. Ditching creates a ditch/ledge in the preparation hole 340 on the model 200. The finish line 500 can be used as base for the ditch. For example, in one arrangement, the ditch is laterally offset from the margin line and/or segmentation line. In some embodiments, the ditching can be made in the CAM-calculation step, but typically the ditching will not be visible for the dental technician in the CAD. But in some embodiments, there can be a graphical visualization of the ditch to simulate the outcome from production. However, in some embodiments, this information will not be used in production. The size and shape of the ditch can be standardized, but in some embodiments, the dimensions of the ditch can be user defined.

In some embodiments, the back of the base plate 230 can have a bar code engraved for the purpose of simplifying handling in manufacturing during packaging of the case. A recycling symbol can be milled and placed on the back of the base plate 230 if desired. In some embodiments, the base plate 230 can also have a company logo and/or manufacturing identification codes engraved.

In some embodiments, a lab technician may desire physical models of the patient's dentition to manufacture a crown, a bridge, or any dental appliance. In a preferred embodiment, the models can include two physical jaw models mounted on an articulator or placed in the correct spatial orientation one against the other. According to this method, the information for the two jaws and their spatial relationship in occlusion is in a digital 3D file. The computer guided milling (or other technology) machine is connected to the computer with the 3D file of the virtual impression, and then a physical model of each one of the jaws is milled from a blank made of acrylic, or other appropriate material taking into consideration also the spatial relation between the two jaws and their occlusion. At this point, the technician has his necessary physical model and can proceed with making the crown or the bridge.

As may be appreciated, the lab technician has to build a crown, a bridge, or other dental appliances, that will have a good fit on the prepared area of the tooth. Contact with the surrounding teeth must be good and in some situations, such as in the case of any prosthesis, there must also be correct contact with teeth on the opposing jaw. If the crown does not fit correctly, the bite will be affected and the crown will not fit comfortably in the mouth.

Based on information from the virtual 3D image, the operator may generate a 3D model of a prosthetic 700, such as a crown to be fitted on a preparation 260 or of a bridge (just placed on multiple preparations) to be fitted on the preparation. In some embodiments, the finish line 500 can be used as the margin line 520 of the crown, or other dental prosthetic 700, which is defined as the apical edge of the prosthetic, as illustrated in FIG. 13. The draw line 600 can be used in designing the dental prosthetic 700 and ensure that the prosthetic 700 can be properly mounted on the preparation 260. In some embodiments, the technician can use the information from the 3D image to generate a digital file on which basis the lab technician, through the use of a computer driven milling machine, may generate a physical crown, bridge or other dental appliances. For example, the construction and fabrication of the crown can be done in a CAD/CAM (Computer-aided-design/Computer-aided-Manufacture) environment, utilizing for example, a CNC (Computer Numerical Control) device.

In some embodiments, the operator can create a physical die using data of the die created in the virtual environment. The physical die can be useful as a physical representation of the preparation 260 to be used in making minor changes or corrections to the prosthetic 700. In this way, the prosthetic can be custom fitted without having the patient with final preparation 260 present.

The fabricated physical model can bear marking or articulator engagement portions, for proper relations. When a negative model is fabricated, it bears a negative marking and/or engagement portions (e.g. depressions), thus providing the positive working model with positive marking and/or engagement portions (e.g. corresponding protrusions).

Figure 14:
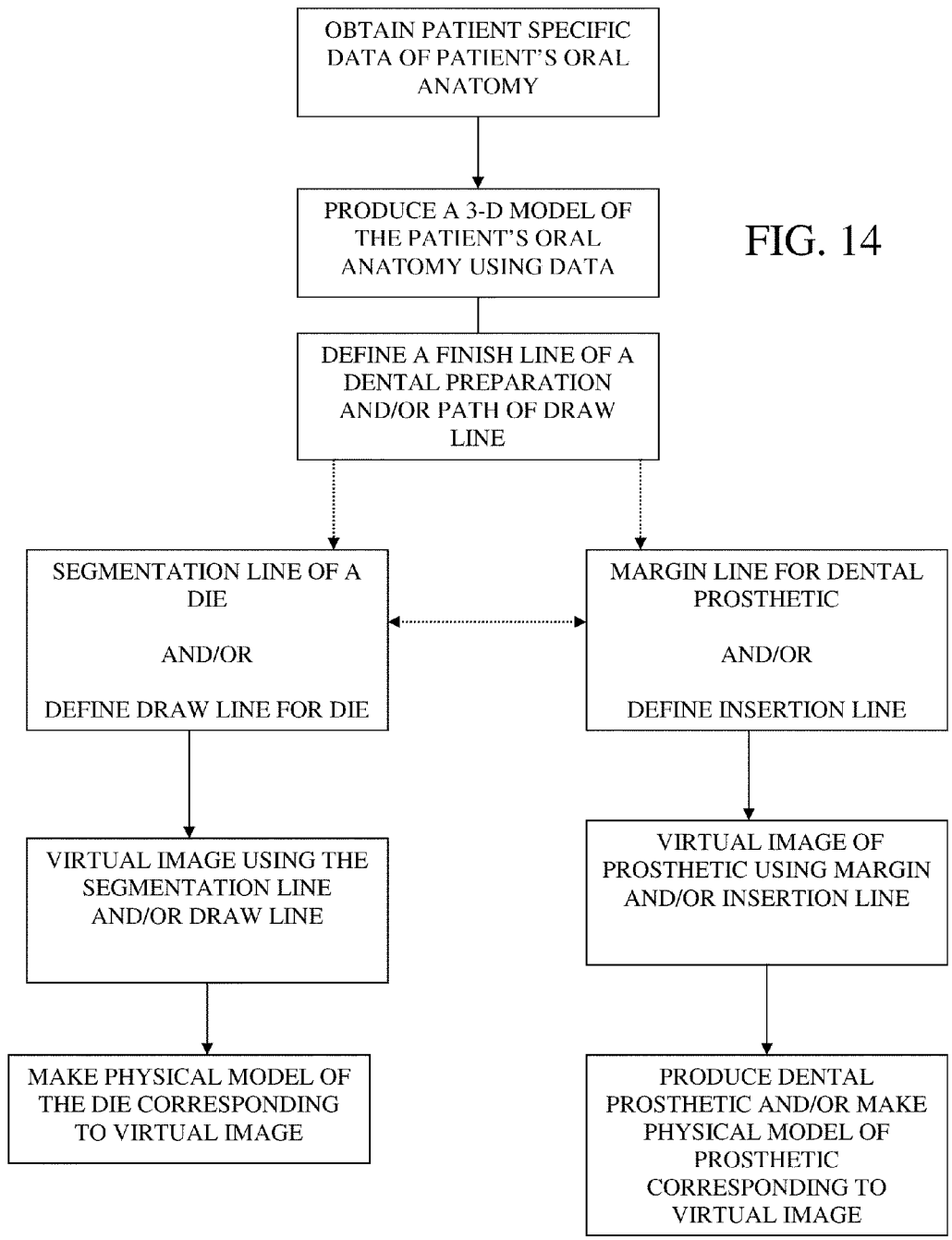
FIG. 14 is a flowchart illustrating the method of making a dental prosthetic, according to an embodiment of the invention.

FIG. 14 is a flowchart illustrating an embodiment method and process for designing and producing a custom dental prosthetic and/or a physical model of a patient's anatomy. As illustrated, the user can obtain patient specific data of the patient's oral anatomy, including surface data of a dental preparation. Then, the user can produce a three-dimensional model of the patient's oral anatomy using the obtained data. A finish line of the dental preparation can be defined in the model, as can a path of draw line. The finish line can be used as the segmentation line for a die and the path of draw line can be used to segment the die. Using the segmentation line and the draw line, a virtual and physical die can be produced. The draw line can be used as the insertion axis line of a dental prosthetic and/or the finish line can be used as a basis for the margin line. Using the insertion axis line and margin line, a virtual and physical dental prosthetic can be produced and fitted on the model. In some embodiments, the finish line can be used as the margin line on the prosthetic. A physical model of the prosthetic can be made for use with the patient's dentition. In some embodiments, a physical model of the die can be made as used for additional adjustments and fitting with the prosthetic. As described above, using patient specific data for one or more components would also include using the specific data as an initial proposal or as a basis for a final data for a component. That is, it is anticipated that the operator can modify the patient specific data as a component is designed. In this manner, by using the patient specific data for one or more components, the number of steps required by the operator can advantageously be reduced.

In the description herein, the die 300 is often described as being created before the prosthetic so that the segmentation line and/or the path of draw line is used for the margin line and/or the insertion line. However, it should be appreciated that the embodiments described herein are not limited to this order. For example, in one embodiment, the virtual prosthetic can be created before or while the virtual die 300 is created. In such an embodiment, the margin line and/or insertion line for the virtual prosthetic can be used to create the segmentation line and/or path of draw line for the virtual die.

Using the finish line 500 of the preparation 260 to create the segmentation line 360 of the die 300 can help create a die 300 that is an accurate representation of the preparation 260 for use in custom fitting the prosthetic 700. An accurate die 300 will help ensure that the prosthetic 700 will sufficiently cover the preparation 260 for a custom and natural looking fit of the prosthetic 700. For example, the operator can ensure that the margins of the prosthetic 700 extend to the segmentation line 360 of the die 300 so that there are no gaps between the gums and the prosthetic 700 when the prosthetic 700 is implanted on the preparation 260, resulting in better aesthetics. In other words, using the finish line 500 as a basis for or as the segmentation line 360, results in better accuracy in fit and finish of the prosthetic 700 because the same data that defines the edges of the preparation 260 is used for the die 300 which is used to ensure the fit of the prosthetic 700. The segmentation line 360 does not need to be defined separately from the finish line 500, which can introduce errors and inaccuracies.

Using the draw line 600 of the die 300 to create the insertion axis line 620 of the prosthetic can help ensure that the prosthetic fits properly onto the preparation 260 without interference with the surface of the preparation 260 or the surrounding teeth. A properly fitting prosthetic 700 can lead to a stronger bond onto the patient's dentition and a longer lasting prosthetic 700. Similar to using the finish line 500, using the draw line 600 results in better accuracy of fit of the prosthetic 700, because the same data that defines the path of draw of the die 300 (or preparation 260) is used to create the insertion axis of the prosthetic 700.

Furthermore, using the finish line 500 and the draw line 600 to create the segmentation line 360 and insertion axis line 620, respectively, advantageously allows the operator to use patient specific data for making the prosthetic 700, resulting in better accuracy of fit. Furthermore, although the finish line 500 and draw line 600 can be defined in one environment or module, it can be transferred and used in another module to define the segmentation line 360 and insertion axis line 620. Thus, although the modules are independent and can be performed at separate locations independently from each other, reusing data from one environment in the other environment links the two environments and helps create a interconnected process for making a custom fitting prosthetic 700.

Although certain embodiments, features, and examples have been described herein, it will be understood by those skilled in the art that many aspects of the methods and devices illustrated and described in the present disclosure may be differently combined and/or modified to form still further embodiments. For example, any one component of the dental prosthetic designing system illustrated and described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

What is claimed is:

1. A method of making a dental component comprising the steps of:
   obtaining, at a computer system, patient specific data regarding a patient's oral anatomy, including three-dimensional surface data of a dental preparation;
   producing, using the computer system, a three-dimensional model of the patient's oral anatomy using the three-dimensional surface data of a dental preparation;
   defining a first aspect of the patient's oral anatomy using the three-dimensional model, wherein the first aspect of the patient's oral anatomy comprises a finish line;
   determining, using the first computer system, a segmentation line for a die using the first aspect of the patient's oral anatomy; and
   determining, using the first computer system, a margin line of a dental prosthetic using the first aspect of the patient's oral anatomy.

2. The method of claim 1, further comprising producing, based on the segmentation line for the die and margin line of the dental prosthetic, a model of the patient's oral anatomy and a final prosthetic.

3. The method according to claim 1, wherein the dental prosthetic is a crown or bridge having a margin line corresponding to the finish line.

4. The method according to claim 1, wherein the step of obtaining patient specific data regarding a patient's oral anatomy comprises an oral scan of the patient's dentition.

5. The method according to claim 1, wherein the step of obtaining patient specific data regarding a patient's oral anatomy comprises scanning an impression of the patient's dentition.

6. The method according to claim 1, wherein the step of determining, using the first computer system, a segmentation line for a die comprises using the first aspect of the patient's oral anatomy as a proposal for the segmentation line for the die.

7. A method of making a dental component comprising the steps of:
   obtaining, at a computer system, patient specific data regarding a patient's oral anatomy, including three-dimensional surface data of a dental preparation;
   producing, using the computer system, a three-dimensional model of the patient's oral anatomy using the three-dimensional surface data of a dental preparation;
   defining a first aspect of the patient's oral anatomy using the three-dimensional model;
   determining, using the first computer system, a segmentation surface for a die using the first aspect of the patient's oral anatomy; and
   determining, using the first computer system, an insertion axis for a dental prosthetic using the first aspect of the patient's oral anatomy;
   wherein the step of defining a first aspect of the patient's oral anatomy comprises defining a draw line.

8. A method of making a dental component comprising:
   obtaining, at a computer system, patient specific data regarding a patient's oral anatomy, including three-dimensional surface data of a dental preparation;

producing, using the computer system, a virtual three-dimensional model of the patient's oral anatomy using the three-dimensional surface data of a dental preparation;

defining a finish line on a virtual model of the preparation;

defining, using the first computer system, a segmentation line for a die using the finish line of the preparation; and defining, using the first computer system, a margin for a dental prosthetic using the finish line.

9. The method according to claim 8, further comprising producing the dental prosthetic.

10. The method according to claim 9, wherein the dental prosthetic is a bridge or a crown having a margin corresponding to the finish line.

11. The method according to claim 8, further comprising the step of manipulating the segmentation line after defining the segmentation line from the finish line.

12. A method of making a dental component comprising:

obtaining, at a computer system, patient specific data regarding a patient's oral anatomy, including three-dimensional surface data of a dental preparation;

producing, using a computer system, a virtual three-dimensional model of the patient's oral anatomy using the three-dimensional surface data of a dental preparation;

defining a draw line using the virtual three-dimensional model;

defining, using the first computer system, an insertion axis line of a dental prosthetic using the draw line; and defining, using the first computer system, a segmentation surface of a die using the draw line.

13. The method according to claim 12, wherein the dental prosthetic is a crown having an insertion axis line corresponding to the draw line.

14. The method according to claim 12, wherein the dental prosthetic is a bridge having an insertion axis line corresponding to the draw line.

15. The method according to claim 12, further comprising the step of manipulating the insertion axis line after defining it from the draw line.

16. A computer system for use in constructing a tooth die and tooth product to be fitted on the tooth die, the computer system comprising:

a scanner for creating digital data representing the surface topology of a physical object;

one or more computers each comprising one or more processors and one or more memories, said one or more computers being configured to:

accept the digital data for use in producing a three-dimensional representation of a patient's dentition;

generate a removable tooth die;

define a finish line of a preparation and superimposing an image of the finish line on an image of the dentition;

define a draw line of the tooth die and superimposing an image of the draw line on an image of the dentition; and accept input from an operator, said input being used by the system to define a segmentation line of the tooth die;

accept input from an operator, said input being used by the system to define an insertion axis line of a dental prosthetic;

wherein the finish line is used as the segmentation line and the draw line is used as the insertion axis line of the dental prosthetic.

17. The computer system of claim 16, wherein a user can manipulate the finish line after it has been defined.

18. The computer system of claim 16, wherein a user can manipulate the draw line after it has been defined.

* * * * *